US00PP37847P3

(12) United States Plant Patent
Grosser

(10) Patent No.: US PP37,847 P3
(45) Date of Patent: Nov. 17, 2026

(54) ***CITRUS* ROOTSTOCK NAMED 'UFR-18'**

(50) Latin Name: ***Citrus* sp.**
Varietal Denomination: UFR-18

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/381,498

(22) Filed: Nov. 6, 2025

(65) Prior Publication Data

US 2026/0130303 P1 May 7, 2026

Related U.S. Application Data

(60) Provisional application No. 63/717,582, filed on Nov. 7, 2024.

(51) Int. Cl.

| | |
|---|---|
| ***A01H 5/08*** | (2018.01) |
| ***A01H 5/02*** | (2018.01) |
| ***A01H 6/78*** | (2018.01) |

(52) U.S. Cl.
USPC ..... Plt./201

CPC ..... *A01H 6/785* (2018.05); *A01H 5/02* (2013.01); *A01H 5/08* (2013.01)

(58) Field of Classification Search
USPC ..... Plt./202, 201
See application file for complete search history.

(56) References Cited

U.S. PATENT DOCUMENTS

| | | | |
|---|---|---|---|
| PP27,277 | P3 | 10/2016 | Grosser |
| PP27,298 | P3 | 10/2016 | Grosser |
| PP27,742 | P3 | 3/2017 | Grosser |
| PP27,745 | P3 | 3/2017 | Grosser |

OTHER PUBLICATIONS

"International Code of Nomenclature for Cultivated Plants," Ninth Edition, Jun. 2016. (3 pages only).*

* cited by examiner

*Primary Examiner* — Susan Mccormick Ewoldt
(74) *Attorney, Agent, or Firm* — Koenig IP Works, PLLC; Katherine Koenig

(57) ABSTRACT

A new and distinct cultivar of orange plant named 'UFR-18', an allotetraploid rootstock with improved disease resistance for use in HLB-endemic areas. This cultivar produces adequate nucellar seed making it amenable to standard nursery propagation practices for uniform liner production. Ungrafted seed trees are especially tolerant of HLB.

12 Drawing Sheets

Genus and species: *Citrus* sp. This new cultivar is a complex *Citrus* hybrid containing *Citrus grandis, Citrus paradisi, Citrus reticulata*, and *Citrus trifoliata.*

Cultivar denomination: 'UFR-18'.

ACKNOWLEDGEMENT OF FEDERAL RESEARCH SUPPORT

N/A.

BACKGROUND OF THE NEW CULTIVAR

The present invention relates to a new and distinct cultivar of orange, botanically known as *Citrus* sp., and hereinafter referred to by the name 'UFR-18'. This *Citrus* sp. is a member of Rutaceae.

The new cultivar of orange 'UFR-18' is an allotetraploid zygotic hybrid ("tetrazyg") derived from a conventional cross of two somatic hybrids previously produced by protoplast fusion. The somatic hybrid seed parent is 'Nova' (not patented) mandarin hybrid+'Hirado Buntan' (not patented) pummelo (zygotic seedling) and the somatic hybrid pollen parent is 'Cleopatra' (not patented) mandarin+'Argentine' (not patented) trifoliate orange. The new cultivar 'UFR-18' is a sibling of 'UFR-1' (U.S. Plant Pat. No. 27,277), 'UFR-2'

(U.S. Plant Pat. No. 27,742), 'UFR-4' (U.S. Plant Pat. No. 27,745), and 'Orange 16' (not patented).

SUMMARY OF THE INVENTION

The new sweet orange cultivar 'UFR-18' has not been observed under all possible environmental conditions. The phenotype of the new cultivar may vary with variations in environment and cultural practices such as temperature, light intensity, fertilization, irrigation, and application of plant growth regulators without any change in genotype.

'UFR-18' rootstock was selected on the basis of its positive reaction to HLB disease (huanglongbing or *Citrus* greening disease) in multiple field trials. Trees grown on this rootstock show an ability to grow off into productive trees in HLB-endemic Florida with no individual protective covers (IPCs) and, in one trial (St. Cloud, Florida), no psyllid control. In a commercial *Citrus* Research and Field Trial (CRAFT), 4-year-old trees with 'OLL-8' sweet orange scions are performing well in an area with heavy *Diaprepes/Phytophthora* complex pressure. In one trial, the new cultivar 'UFR-18' out-performed other top commercial rootstocks in a wet flatwoods growing block, including 'US-942' (not patented), 'US-812' (not patented), 'x639' (not patented), 'UFR-4' (U.S. Plant Pat. No. 27,745), and 'UFR-5' (U.S. Plant Pat. No. 27,298). In another trial, the new cultivar 'UFR-18' performed very well under heavy HLB-pressure that included many rootstocks, planted near Babson Park, Florida. Seven-year-old trees with 'OLL-10' (not patented) sweet orange as the scion are also performing well in in other areas of Florida. Although trees grafted to 'UFR-18' rootstock grow off quickly, trees grow to medium size. Some roguing is required in the nursery, but this selection produces adequate nucellar seed making it amenable to standard nursery propagation practices for uniform liner production. Ungrafted seed trees are especially tolerant of HLB.

There are limited replicated field trial data regarding the performance of 'UFR-18' rootstock. However, trees grafted with 'Valencia' (not patented) and planted in 2008 in St. Cloud, Florida, grown with no psyllid control, are still productive. Seven-year-old trees with 'UFR-18' rootstock and 'OLL-10' scion planted near Lake Alfred, Florida, are also healthy and productive. One 4-tree plot was observed in Dundee, Florida, which did not perform well, but no specific reason for this was determined. Overall, 'UFR-18' rootstock appears to be at least as strong as any available commercial rootstocks in HLB-endemic Florida.

The new cultivar 'UFR-18' can be compared to the commercial cultivar 'UFR-4'. The new cultivar 'UFR-18' has similar performance, but is stronger in areas impacted by the sugar cane root weevil (*Diaprepes abbreviates*), an insect pest that damages *Citrus* roots.

DESCRIPTION OF THE FIGURES

This new sweet orange cultivar 'UFR-18' is illustrated by the accompanying photographs which show the tree's form, foliage and fruit. The colors shown are as true as can be reasonably obtained by conventional photographic procedures. The photographs are of a tree approximately 6 years old.

DETAILED BOTANICAL DESCRIPTION OF THE CULTIVAR

Botanical Description

Figure 1:
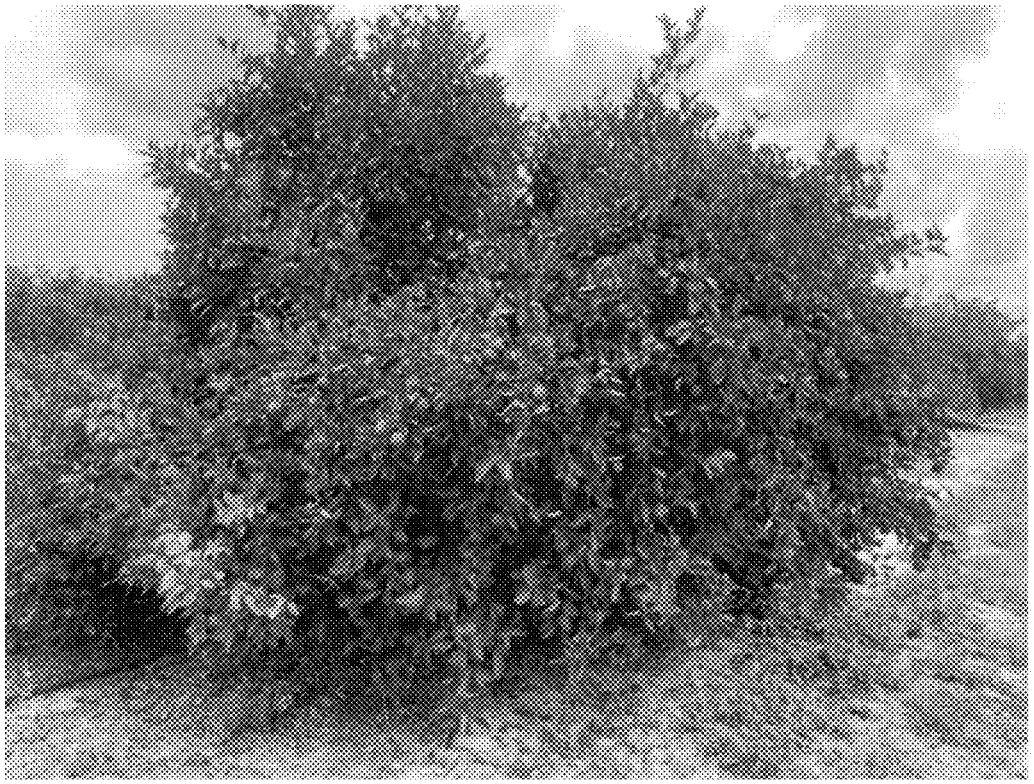
FIG. 1 shows HLB-tolerant seed tree of the new cultivar 'UFR-18' planted in Lake Alfred, Florida.
Figure 2:
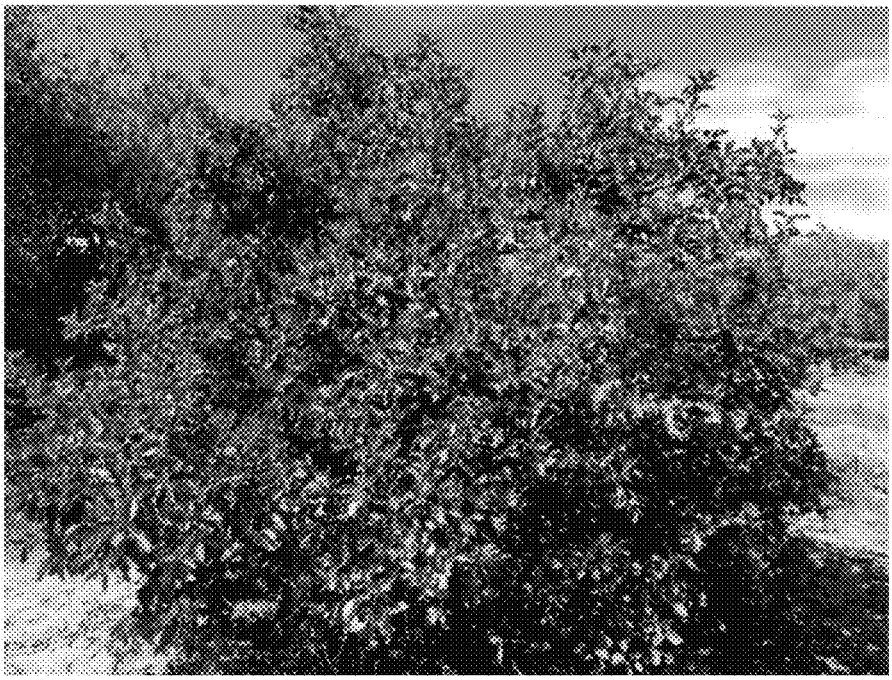
FIG. 2 shows a seed tree of the new cultivar 'UFR-18' planted in Lake Alfred, Florida.
Figure 3:
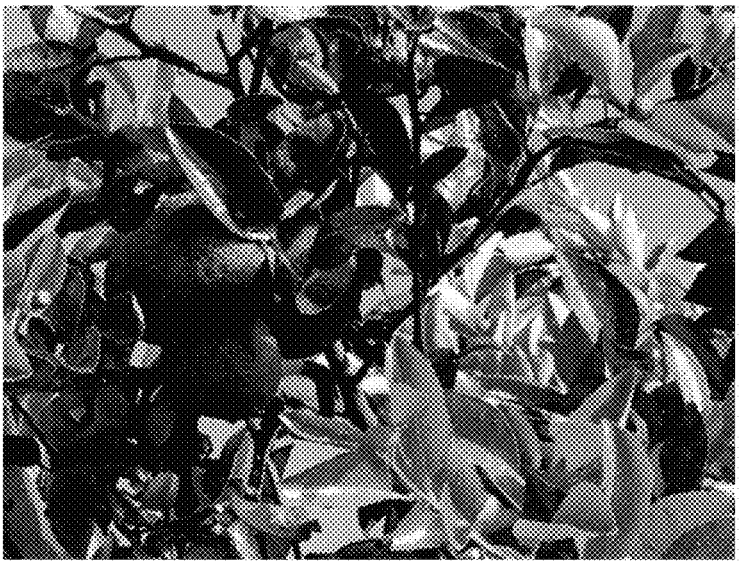
FIG. 3 shows seed fruit cluster in a seed tree of the new cultivar 'UFR-18'.
Figure 4:
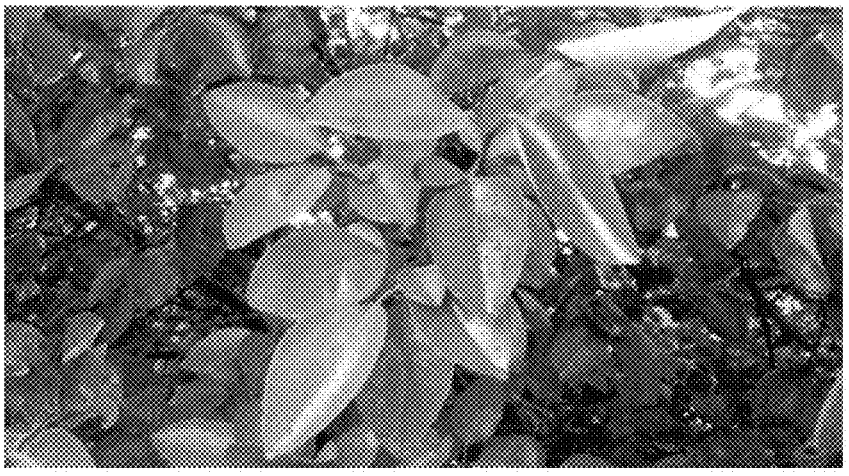
FIG. 4 shows new leaf flush in a seed tree of the new cultivar 'UFR-18'.
Figure 5:
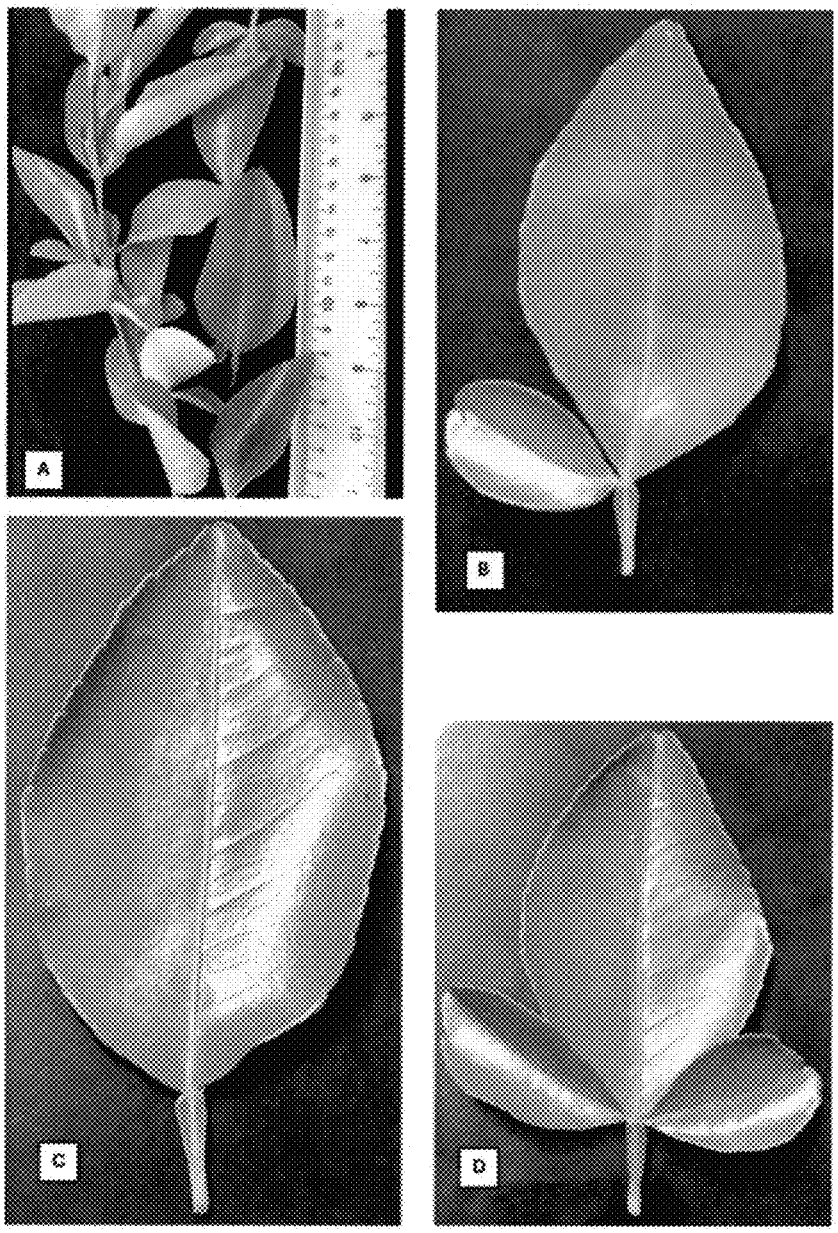
FIG. 5 shows leaf morphology of the new cultivar 'UFR-18'. Image A shows a vegetative flush exhibiting the coexistence of three distinct leaf types on a single branch, alongside a metric ruler for size reference; Image B shows a bifoliate leaf structure; Image C shows a simple (unifoliate) leaf structure; and Image D shows a trifoliate leaf structure.
Figure 6:
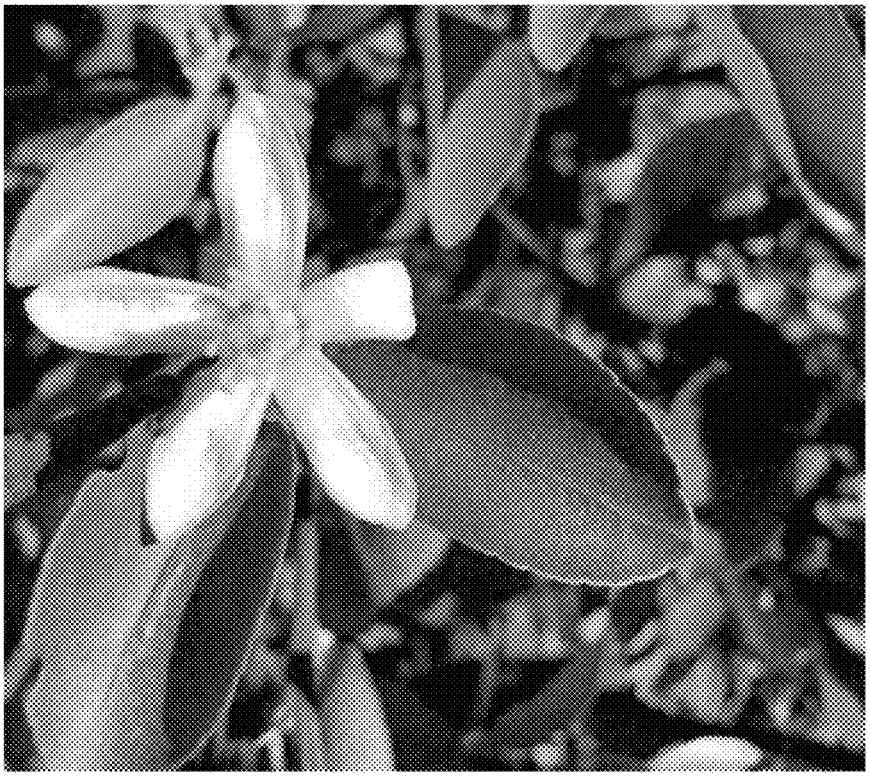
FIG. 6 shows flower morphology of the new cultivar 'UFR-18'.
Figure 7:
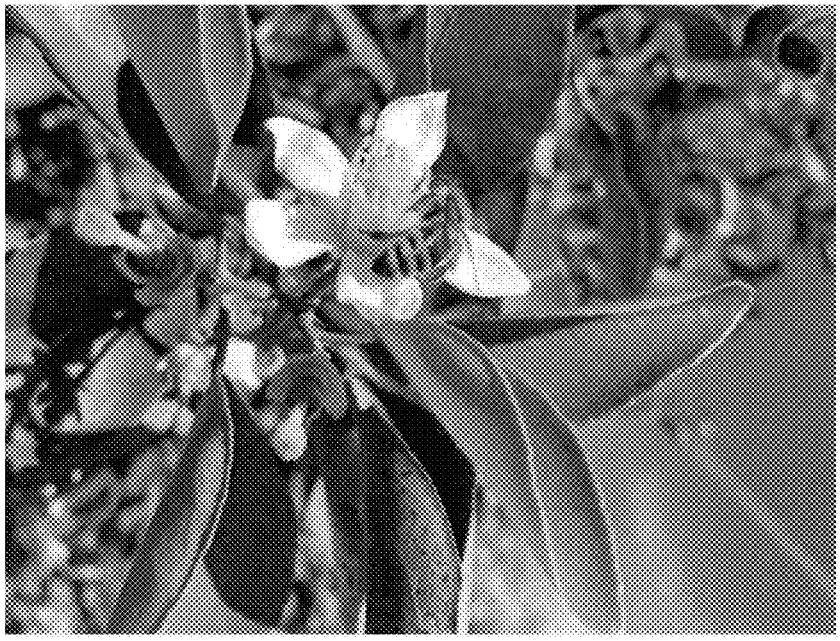
FIG. 7 shows flower and fruit setting of the new cultivar 'UFR-18'.
Figure 8:
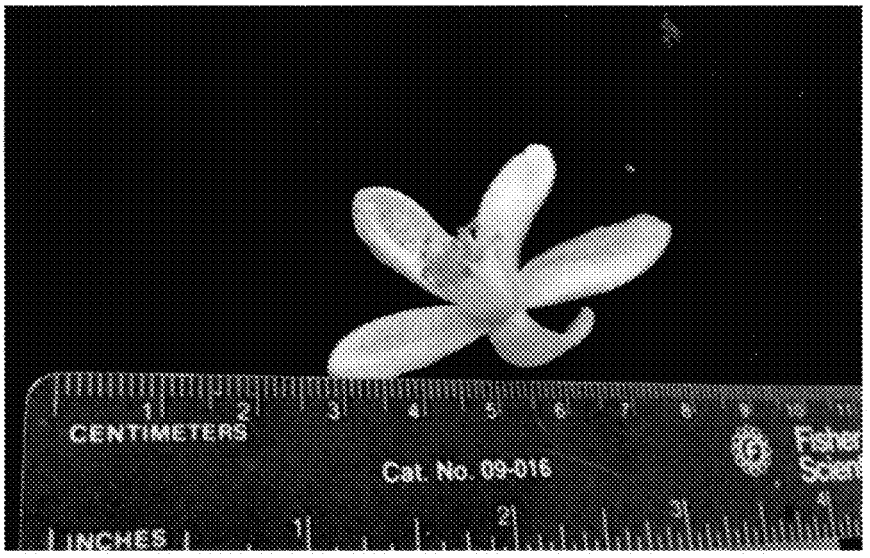
FIG. 8 shows flower size of the new cultivar 'UFR-18', with a ruler shown for size reference.
Figure 9:
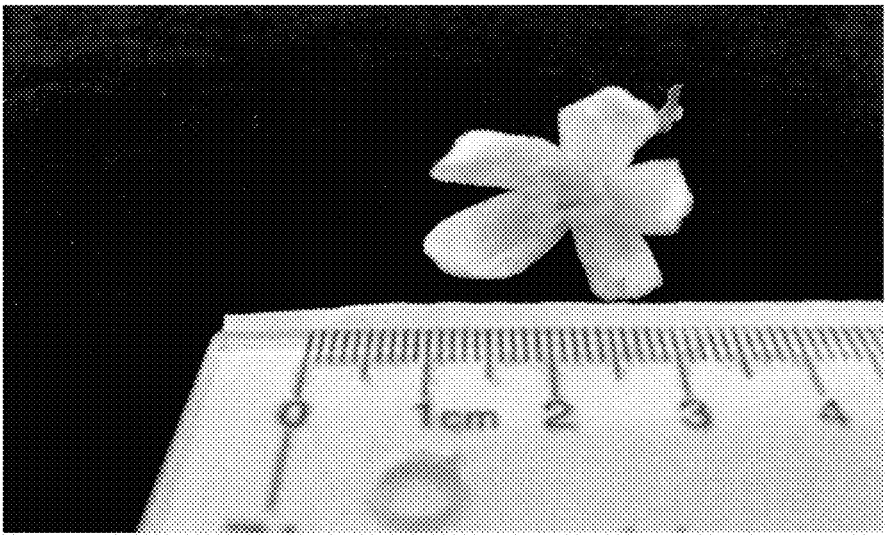
FIG. 9 shows a flower of the new cultivar 'UFR-18', showing dehiscing pollen with a ruler shown for size reference.
Figure 10:
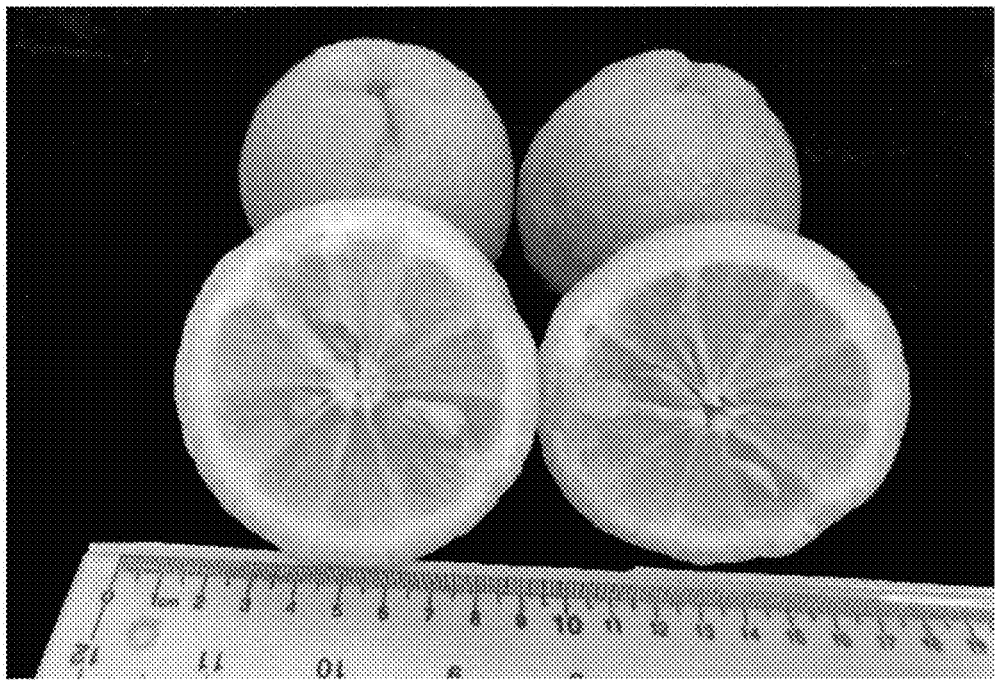
FIG. 10 shows a cut seed fruit of the new cultivar 'UFR-18'.
Figure 11:
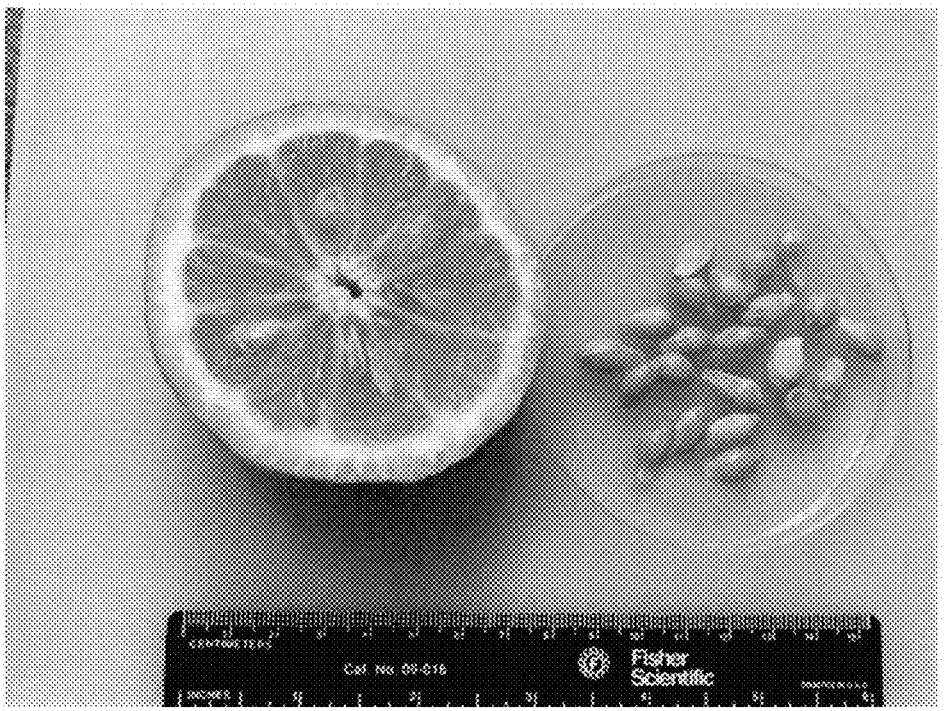
FIG. 11 shows a cut seed fruit and extracted polyembryonic seed of the new cultivar 'UFR-18'.
Figure 12:
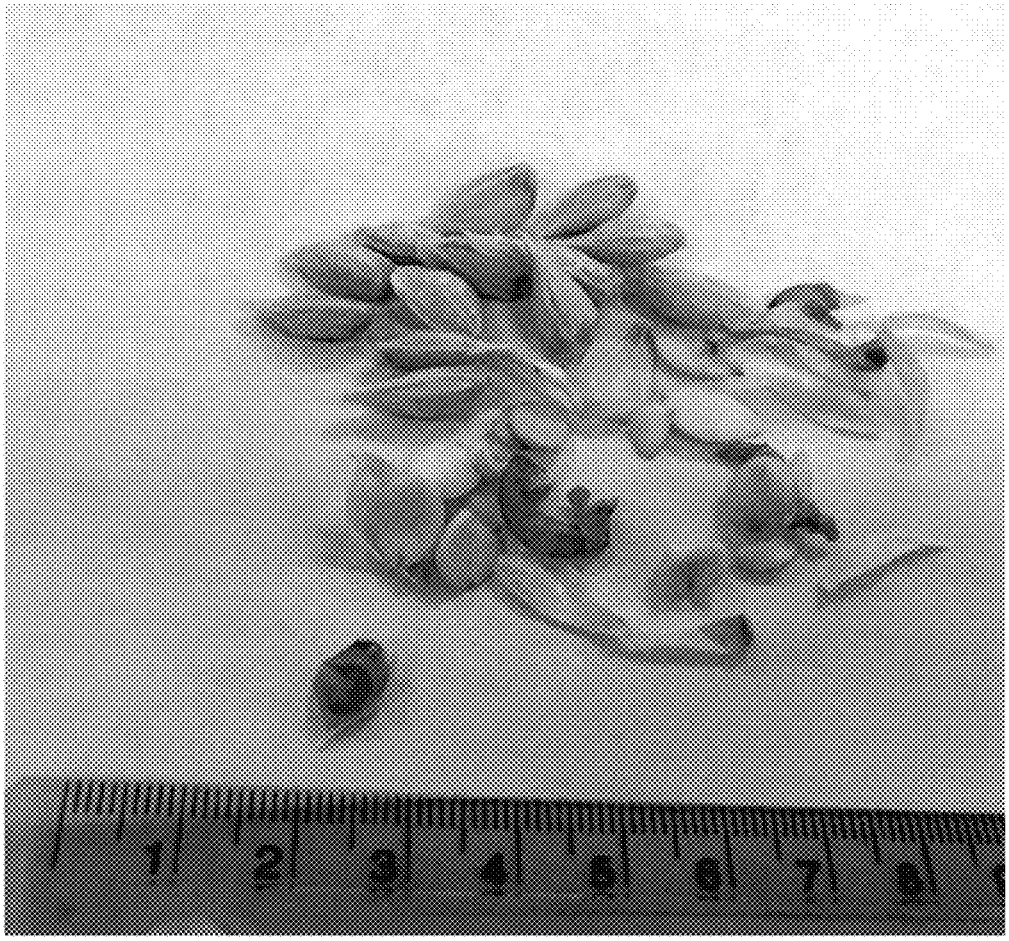
FIG. 12 shows typical polyembryonic seed of the new cultivar 'UFR-18'.
Figure 13:
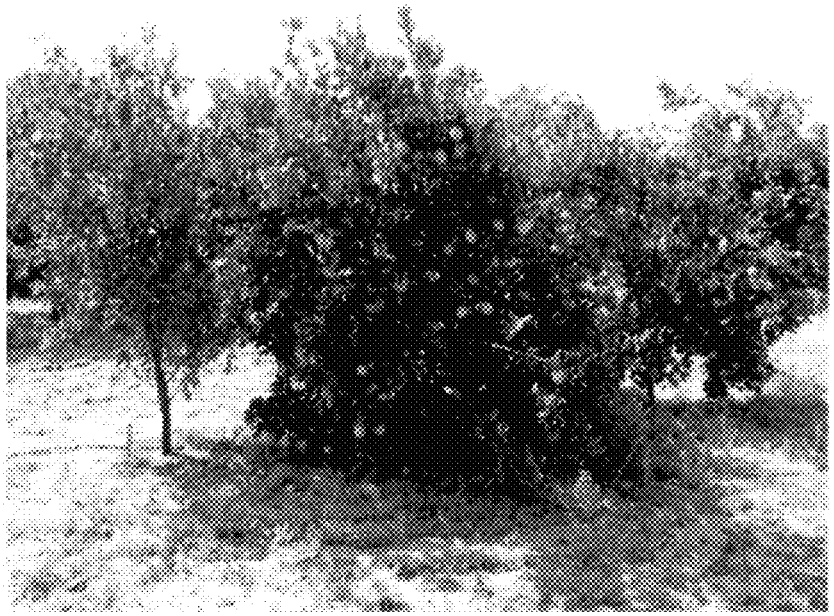
FIG. 13 shows 'Valencia' grown on 'UFR-18' rootstock in St. Cloud, Florida, planted between two 'Valencia' /rough lemon trees.
Figure 14:
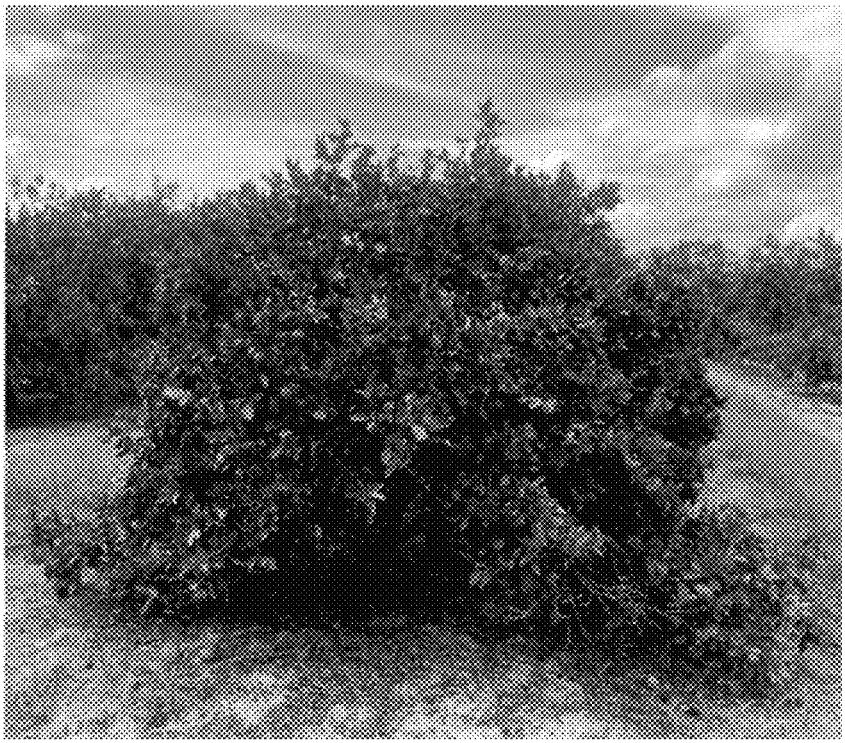
FIG. 14 shows 'OLL-10' sweet orange grown on 'UFR-18' rootstock near Lake Alfred, Florida.
Figure 15:
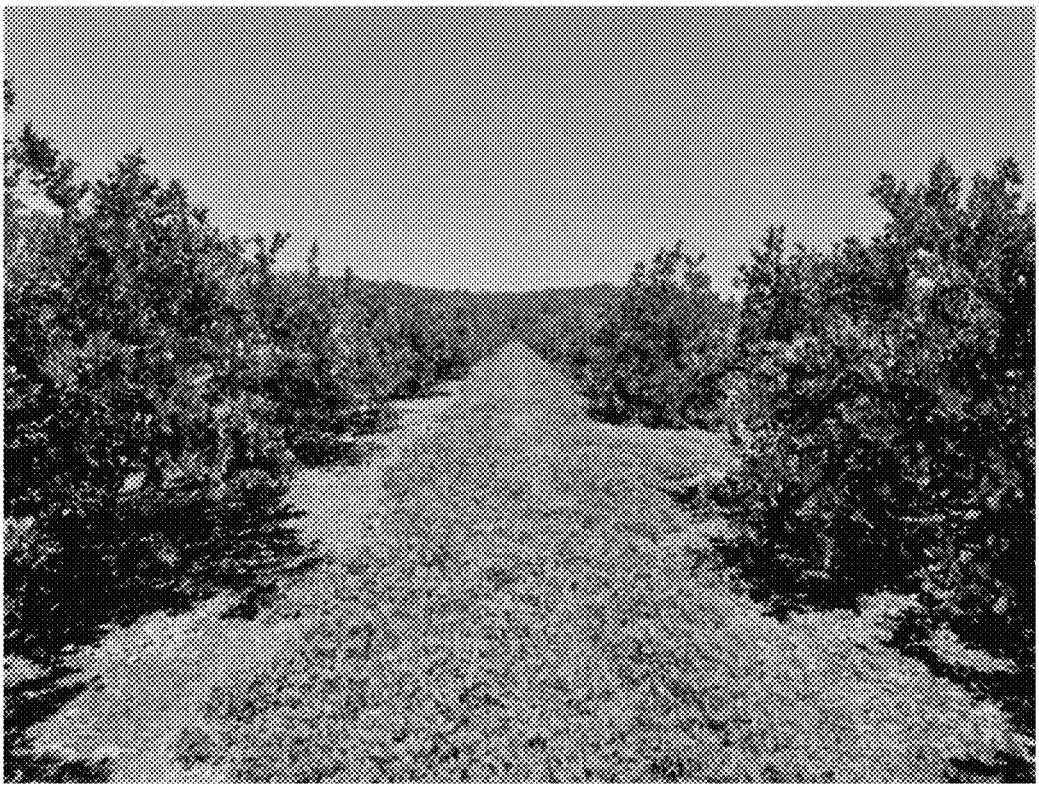
FIG. 15 shows 'OLL-8' sweet orange grown on 'UFR-18' rootstock, 3.5-year-old planted commercial grove with heavy *Diaprepes/Phytophthora* pressure.
Figure 16:
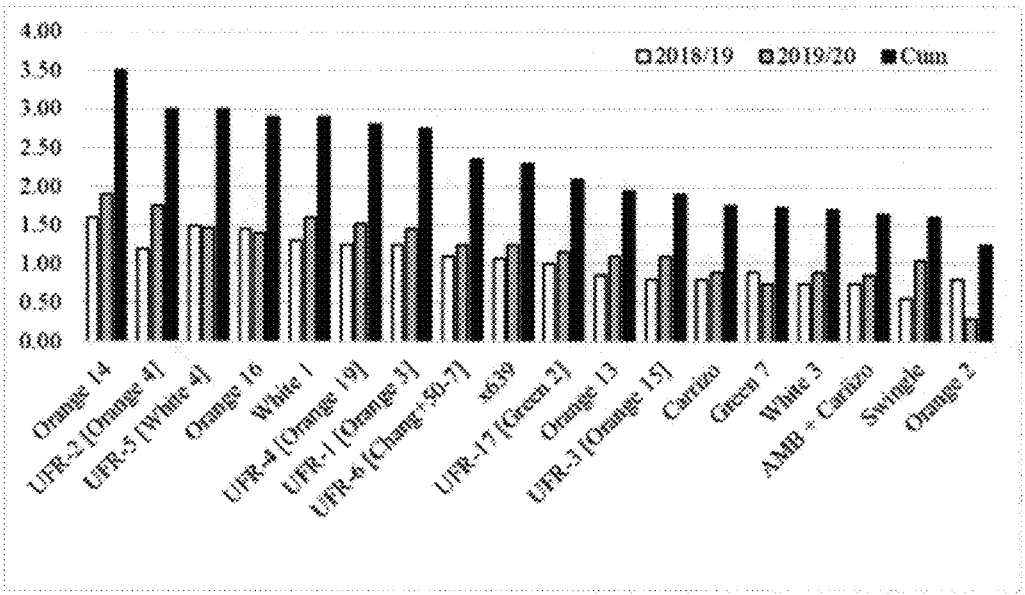
FIG. 16 is a graph showing mean yield and cumulative yield (boxes/tree) by rootstock across all scions (8 OLL clones), sorted by cumulative yield. Trees were planted in summer of 2013 in St. Cloud, Florida, and grown with no psyllid control.

Botanical classification:

*Family*.—Rutaceae.

*Botanical name*.—*Citrus* sp. This new cultivar is a complex *Citrus* hybrid containing *Citrus grandis, Citrus paradisi, Citrus reticulata*, and *Citrus trifoliata*.

*Common name*.—Tetrazyg rootstock.

*Cultivar*.—'UFR-18'.

Parentage: The somatic hybrid seed parent is 'Nova' mandarin hybrid+'Hirado Buntan' pummelo (zygotic seedling) and the somatic hybrid pollen parent is 'Cleopatra' mandarin+'Argentine' trifoliate orange.

Tree:

*Ploidy*.—Tetraploid.

*Size*.—Medium, moderate.

*Width across the row*.—3.5 meters on average.

*Width down row*.—3.5 to 4 meters on average.

*Tree Height*.—3.5 meters on average

*Tree spread*.—Up to 4.00 meter.

*Vigor*.—Moderate to vigorous

*Density*.—Canopies are quite dense.

*Tree shape* (*form*).—The shape of the tree is obloid with lateral branches.

*Tree diameter*.—4 meters on average.

*Growth habit* (*current season*).—Mostly lateral with some upright growth.

Trunk:

*Trunk diameter*.—Approximately 10.5 cm in diameter at 30 cm above from ground in a 6-year-old tree.

*Trunk texture*.—Smooth.

*Trunk bark color*.—RHS N199A (Grey-Brown).

Branches:

*Branch length*.—2.5 to 3 meters on average

*Crotch angle*.—Acute (less than 90 degrees).

*Branch texture*.—Relatively smooth with some thorns.

*Branch color*.—RHS 137A (Green Group) with some RHS 137B (Green Group).

*Spine size*.—10-20 mm on average.

*Spine color*.—RHS 137A (Green Group) with some RHS N199B (Greyed-Brown) based on the age of the branch Leaves:

*Size* (*lamina average*).—Length: 90 mm on average. Width: 50 mm on average L/W ratio: 1.8.

*Thickness*.—Medium (approximately 0.23 mm).

*Type*.—The tree has three types of leaves: unifoliate, bifoliate and trifoliate. Trifoliate leaves are most common in newly germinated seedlings. As trees grow older, most leaves are unifoliate, with fewer trifoliate and bifoliate leaves being present.

*Shape*.—Elliptical.

*Apex*.—Retuse.

*Base*.—Acute.

*Margin*.—Dentate.

*Surface*.—Upper surface: Smooth. Lower surface: Smooth with the medium veins that are pinnately netted.

*Color*.—Upper surface (adaxial): RHS 137A (Green Group). Lower surface (abaxial): RHS 137B (Green Group).

*Petiole*.—Shape and attachment: Brevipetiolate (shorter than leaf lamina); junction between petiole and lamina is articulate. Width: Narrow. Shape (petiole wing): Obovate. Length: 18 mm to 22 mm. Width: 3 mm to 3.2 mm. Color: RHS 137A (Green).

Flowers:

*Type*.—Hermaphrodite.

*Flowers bearing*.—Single or cluster. Branches have flowers grown in clusters. Each cluster consists of 2-5 flowers. Individual flowers grow from leaf terminals and leaf axillaries.

*Flower diameter*.—Fully open flower with average diameter of 25 mm to 35 mm.

*Flower depth*.—Typical flower with average depth of 20 mm.

*Flower blooming period*.—First bloom observed: Late February 2024. Full bloom observed: Mid-March 2024.

*Flower bud size*.—Length: Initial visible flower bud is approximately 2 mm in length; mature flower bud is approximately 20 mm in length. Diameter: Initial visible flower bud is approximately 2 mm in diameter; mature flower bud is approximately 5.5 mm in diameter. Shape: Initial visible flower bud has a round ball shape; mature flower bud has an elongated olive shape. Color: RHS 144C (Yellow-Green) for initial visible flower bud; RHS NN 155A (White) for mature flower bud.

*Petals*.—Number: 5 per flower. Shape: Flat spatula shaped. Length: 22 mm on average. Width: 6 mm on average. Apex shape: Smooth, acute shaped. Base shape: Even obtuse. Color: Upper surface is RHS NN 155A (White); lower surface is RHS NN 155C (White). Margin: Smooth.

*Sepal*.—Number: 3-5 per flower. Shape: Delta shaped with acute angle at apex. Length: 3 mm on average. Width: 3.5 mm on average. Apex shape: Triangle shaped. Margin: Smooth. Color: RHS 1A (Green-Yellow). Fragrance: Moderately fragrant.

*Pedicel*.—Length: 7 mm to 8 mm. Diameter: 2 mm on average. Color: RHS 1B (Green-Yellow).

*Stamen*.—Number: 22 per flower on average. Length: 13 mm on average.

*Anther*.—Length: 2.5 mm on average. Width: 1.5 mm on average. Color: RHS 10A (Yellow). Pollen amount: Abundant. Pollen color (general): Bright yellow, RHS 17A (Yellow).

*Pistil*.—Number: 1. Length: 12.5 mm on average. Color: RHS 153B (Yellow-Green). Style length: 9.5 mm on average. Style diameter: 1 mm on average. Style color: RHS 144A (Yellow-Green). Ovary shape: Oval. Ovary diameter: 2.5 mm on average. Ovary color: RHS N 144D (Yellow-Green).

Fruit:

*Fruit parthenocarpy*.—Yes.

*Size*.—Uniform. Tall: 75 mm to 82 mm on average. Diameter: 75 mm on average.

*Average weight* (*per individual fruit*).—194.73 grams.

*Shape*.—Round.

*Shape* (*cross-section*).—Round.

*Apex*.—Truncated.

*Base*.—No neck, slightly rough peel surface.

*Harvest*.—First pick: Around September. Last pick: Around December.

*Fruit stem* (*short stem connecting the fruit*).—Length: 8.5 mm on average. Diameter: 3.5 mm on average. Color: RHS 198D (Greyed-Green).

*Rind*.—Adherence: Adherence between albedo (mesocarp) and flesh (endocarp) is medium. Thickness: 4 mm on average. Texture: Firmed. Color: Flavedo (epicarp): RHS 163B (Greyed-Orange). Albedo (mesocarp): RHS NN 150B (White). Style end: Closed. Rind oil cell density: Approximately 180 cells/cm$^2$.

*Flesh*.—Number of segments: 10-12 segments per fruit. Segment walls: Medium. Juice: Abundant. Color: RHS 163C (Greyed-Orange) with some RHS 10A (Yellow Group). Texture: Soft. Vesicles: Medium thickness. Length: 13 mm to 15 mm on average. Diameter: 2.5 mm to 3 mm on average.

*Seeds*.—Type: Polyembryonic. Number: 18 to 22 per fruit. Shape: Seed shapes are uniform, elongated oval shape. Size: Length: 15 mm to 17 mm. Width: 9 mm to 10 mm. Seed coat color: RHS 158B (Yellow-White). Outer Surface: RHS 161B (Greyed-Yellow). Inner surface: RHS 165C (Greyed-Orange). Cotyledon color: RHS 157D (Green-White).

TABLE 1

St. Cloud Demonstration Planting: 2018/2019 and 2019/2020 PS (lbs. solids)/tree and 2-year cumulative yield by rootstock for 'OLL-8' sweet orange. Trees were planted in summer of 2013 in St. Cloud, Florida, and grown with no psyllid control.

| | PS/Tree | | |
|---|---|---|---|
| Rootstock | 2018/2019 | 2019/2020 | Cumulative |
| 'UFR-18' | 13.1 | 17.0 | 30.1 |
| 'UFR-5' (White 4) | 17.1 | 12.9 | 30.1 |
| 'UFR-1' (Orange 3) | 13.2 | 12.3 | 25.6 |
| 'UFR-2' (Orange 4) | 11.4 | 13.9 | 25.4 |
| 'Orange 16' | 13.3 | 11.2 | 24.5 |
| 'White 1' | 11.6 | 11.1 | 22.7 |
| 'UFR-4' (Orange 19) | 8.6 | 11.6 | 20.1 |
| 'UFR-6' ('Chang' + '50-7') | 9.6 | 8.3 | 17.9 |
| 'x639' | 8.7 | 7.9 | 16.6 |
| 'Carrizo' | 9.3 | 6.2 | 15.5 |
| 'Orange 2' | 8.5 | 6.8 | 15.3 |
| 'Swingle' | 6.9 | 8.2 | 15.1 |
| 'Orange 13' | 6.7 | 6.0 | 12.6 |

TABLE 1-continued

St. Cloud Demonstration Planting: 2018/2019 and 2019/2020 PS (lbs. solids)/tree and 2-year cumulative yield by rootstock for 'OLL-8' sweet orange. Trees were planted in summer of 2013 in St. Cloud, Florida, and grown with no psyllid control.

| | PS/Tree | | |
|---|---|---|---|
| Rootstock | 2018/2019 | 2019/2020 | Cumulative |
| 'White 3' | 5.1 | 7.5 | 12.6 |
| 'UFR-3' (Orange 15) | 5.9 | 6.6 | 12.4 |
| 'UFR-17' (Green 2) | 6.5 | 5.6 | 12.0 |

TABLE 1-continued

St. Cloud Demonstration Planting: 2018/2019 and 2019/2020 PS (lbs. solids)/tree and 2-year cumulative yield by rootstock for 'OLL-8' sweet orange. Trees were planted in summer of 2013 in St. Cloud, Florida, and grown with no psyllid control.

| | PS/Tree | | |
|---|---|---|---|
| Rootstock | 2018/2019 | 2019/2020 | Cumulative |
| 'AMB' + 'Carrizo' | 3.2 | 3.5 | 6.7 |
| 'Green 7' | 3.5 | N/A | 3.5 |

The invention claimed is:

1. A new and distinct *Citrus* rootstock named 'UFR-18' as illustrated and described herein.

* * * * *